US011488701B2

(12) United States Patent
Bettencourt Da Silva et al.

(10) Patent No.: US 11,488,701 B2
(45) Date of Patent: Nov. 1, 2022

(54) COGNITIVE HEALTH STATE LEARNING AND CUSTOMIZED ADVICE GENERATION

(71) Applicant: INTERNATIONAL BUSINESS MACHINES CORPORATION, Armonk, NY (US)

(72) Inventors: Joao H. Bettencourt Da Silva, Dublin (IE); Spyros Kotoulas, Dublin (IE); Natasha Mulligan, Dublin (IE); Marco Luca Sbodio, Castaheany (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 921 days.

(21) Appl. No.: 15/700,448

(22) Filed: Sep. 11, 2017

(65) Prior Publication Data

US 2019/0080055 A1 Mar. 14, 2019

(51) Int. Cl.
| | |
|---|---|
| *G16H 20/30* | (2018.01) |
| *G16H 40/63* | (2018.01) |
| *G16H 50/70* | (2018.01) |
| *G16H 20/70* | (2018.01) |
| *G16H 50/20* | (2018.01) |
| *G06N 20/00* | (2019.01) |
| *G16H 50/30* | (2018.01) |
| *G16H 20/60* | (2018.01) |

(52) U.S. Cl.
CPC ............ *G16H 20/30* (2018.01); *G06N 20/00* (2019.01); *G16H 20/70* (2018.01); *G16H 40/63* (2018.01); *G16H 50/20* (2018.01); *G16H 50/70* (2018.01); *G16H 20/60* (2018.01); *G16H 50/30* (2018.01)

(58) Field of Classification Search
CPC ...... G06F 19/34; G06F 19/3475; G16H 20/30; G16H 50/70; G16H 50/20; G16H 40/63; G16H 20/70; G16H 50/30; G16H 20/60
See application file for complete search history.

(56) References Cited

U.S. PATENT DOCUMENTS

| | | | |
|---|---|---|---|
| 2011/0184250 A1 | 7/2011 | Schmidt et al. | |
| 2015/0125832 A1* | 5/2015 | Tran ................... | G09B 19/0092 434/127 |
| 2015/0276419 A1 | 10/2015 | Hashem et al. | |
| 2016/0019666 A1* | 1/2016 | Amarasingham ...... | G16H 40/20 705/3 |
| 2017/0039339 A1 | 2/2017 | Bitran et al. | |

(Continued)

FOREIGN PATENT DOCUMENTS

WO    WO-2017136336 A1 *  8/2017  ............. A61B 5/082

OTHER PUBLICATIONS

E. Balandina, S. Balandin, Y. Koucheryavy and D. Mouromtsev, "IoT Use Cases in Healthcare and Tourism," 2015 IEEE 17th Conference on Business Informatics, 2015, pp. 37-44, doi: 10.1109/CBI.2015.16. (Year: 2015).*

*Primary Examiner* — James D. Rutten
(74) *Attorney, Agent, or Firm* — Griffiths & Seaton PLLC

(57) ABSTRACT

Embodiments for generating personalized advice to a user by a processor. A health state of a user may be learned from feedback information collected from a plurality of data sources for providing one or more customized communications. One or more customized communications may be provided to a user to alter one or more activities of the user so as to avoid one or more possible negative impacts upon the health state of the user.

18 Claims, 7 Drawing Sheets

(56) References Cited

U.S. PATENT DOCUMENTS

2017/0039480 A1    2/2017  Bitran et al.
2017/0311132 A1*  10/2017  Drayson ................. H04W 4/42
2018/0060500 A1*  3/2018  Ni .......................... G16H 10/65

* cited by examiner

COGNITIVE HEALTH STATE LEARNING AND CUSTOMIZED ADVICE GENERATION

BACKGROUND OF THE INVENTION

Field of the Invention

The present invention relates in general to computing systems, and more particularly to, various embodiments for cognitive health state learning and customized advice generation by a processor.

Description of the Related Art

In today's society, consumers, business persons, educators, and others use various computing network systems with increasing frequency in a variety of settings. The advent of computers and networking technologies have made possible the increase in the quality of life while enhancing day-to-day activities. For example, many individuals require extensive use of technology relating to the health and the medical field.

Computing systems can include an Internet of Things (IoT), which is the interconnection of computing devices scattered across the globe using the existing Internet infrastructure. IoT devices may be embedded in a variety of physical devices or products. As great strides and advances in technologies come to fruition, the greater the need to make progress in these systems advantageous for efficiency and safety such as, for example, for using the vast amount of available data to recognize and mitigate adverse impacts on a well-being or health of a person.

SUMMARY OF THE INVENTION

Various embodiments for learning a health state of a user and generating personalized advice relating to the learned health state using one or more processors, are provided. In one embodiment, by way of example only, a method for generating personalized advice, again by a processor, is provided. A health state of a user may be learned from feedback information collected from a plurality of data sources for providing one or more customized communications. One or more customized communications may be provided to a user to alter one or more activities of the user so as to avoid one or more possible negative impacts upon the health state of the user.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE DRAWINGS

Figure 1:
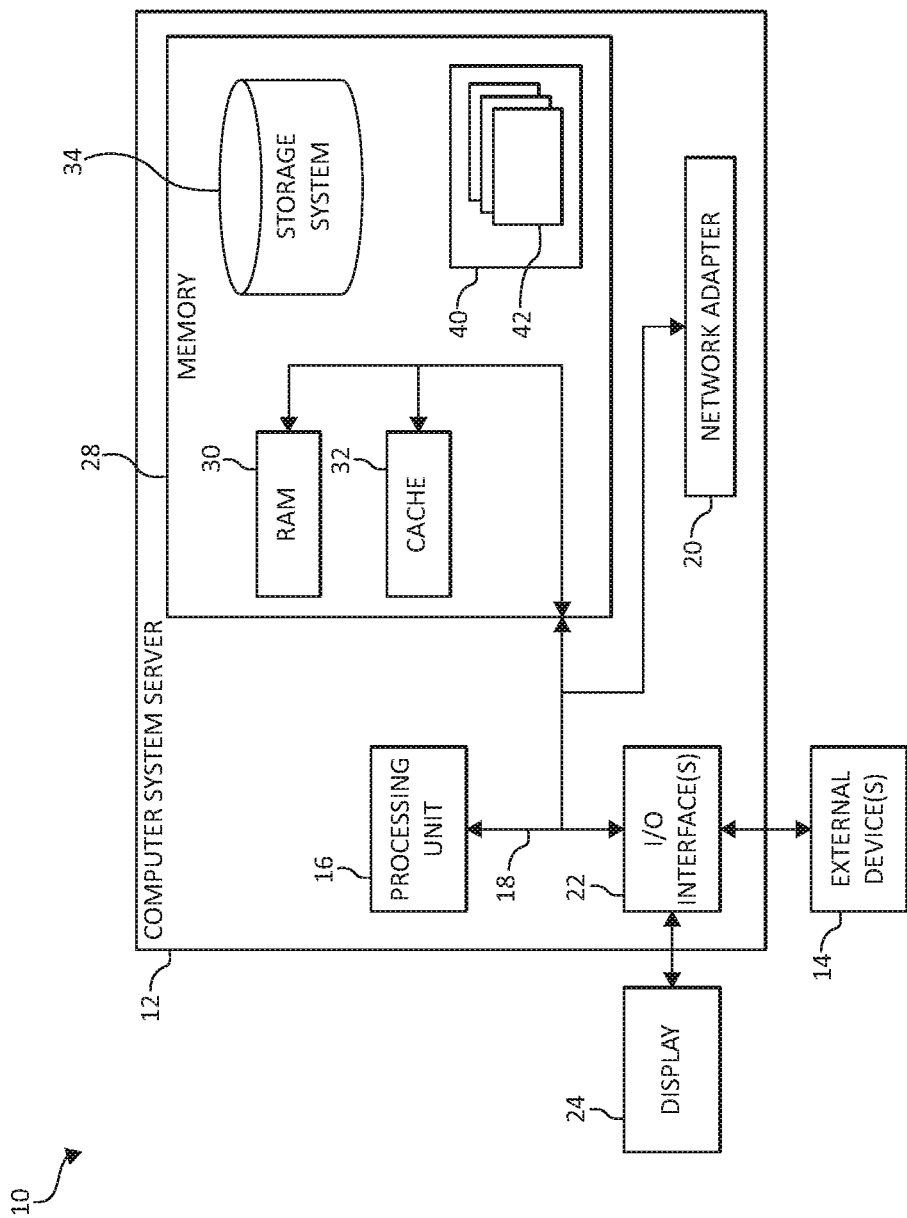
FIG. 1 is a block diagram depicting an exemplary computing node according to an embodiment of the present invention.

Computing systems may include large scale computing called "cloud computing," in which resources may interact and/or be accessed via a communication system, such as a computer network. Resources may be software-rendered simulations and/or emulations of computing devices, storage devices, applications, and/or other computer-related devices and/or services run on one or more computing devices, such as a server. For example, a plurality of servers may communicate and/or share information that may expand and/or contract across servers depending on an amount of processing power, storage space, and/or other computing resources needed to accomplish requested tasks. The word "cloud" alludes to the cloud-shaped appearance of a diagram of interconnectivity between computing devices, computer networks, and/or other computer related devices that interact in such an arrangement.

Additionally, the Internet of Things (IoT) is an emerging concept of computing devices that may be embedded in objects, especially appliances, and connected through a network. An IoT network may include one or more IoT devices or "smart devices", which are physical objects such as appliances with computing devices embedded therein. Many of these objects are devices that are independently operable, but they may also be paired with a control system or alternatively a distributed control system such as one running over a cloud computing environment.

The prolific increase in use of IoT appliances in computing systems, particularly within the cloud computing environment, in a variety of settings provide various beneficial uses to a user. For example, as the demand for and access to data continues to expand in society, consumers of information content, particularly individuals desiring to make well-informed decisions regarding a medical condition or health state, continue to increase. The openness of the internet with the ever-increasing availability of a variety of types of computing devices, IoT devices, and the cloud computing environment for viewing, interacting, or engaging with information, provides the ability of users to have continuous access to information content relating to a variety of settings. Consider for example, a person having a medical condition such as, for example, an allergy to pollen. If, for example, the person has a scheduled event (e.g., an outdoor activity), the person may desire to know that the scheduled event should be avoided, rescheduled, or adjusted to accommodate the medical condition. Thus, a need exists to detect one or more activities or events that may have an adverse or negative impact on the person's well-being or medical condition.

Accordingly, the present invention provides for learning a health state of a user and generating personalized advice relating to the learned health state to avoid possible negative impacts upon the health state of a user/patient using one or more processors. In one embodiment, by way of example only, a health state of a user is learned from feedback information collected from a plurality of data sources for providing one or more customized communications. One or more customized communications may be provided to a user to alter one or more activities of the user so as to avoid one or more possible negative impacts upon the health state of the user.

In one aspect, cognitively reasoning and interacting may be performed with the user for collecting the feedback information, and the feedback information may be acquired using one or more IoT devices during the cognitive reasoning and interaction with the user.

A machine learning mechanism, employing one or more predictive models, may use the feedback information to learn the health state. In one aspect, the health state may include at least one or more medical conditions, a well-being (e.g., subjective well-being "SWB", emotional well-being, mental well-being, physical well-being, or an overall well-being) of the user, an emotional state of the user, biometric data, behavior patterns, a health profile of the user, or a combination thereof. In one aspect, well-being may be generally described as a normal/standardized or satisfactory condition of existence of the user or a state characterized by health, happiness, emotional stability, mental stability, physical stability, or success. As one of ordinary skill in the art will appreciate, "well-being" may be dependent on a number of factors, including such factors as medical condition, emotional stability, mental stability, physical stability, financial stability, a degree or level of happiness, or other factors that may be learned. A well-being of a user/patient may be defined. For example, a knowledge base or ontology may be used to define a well-being for a user/patient and may include defining and/or indicating one or more correlations between a health state, a plurality of states, medical conditions, activities of daily living (ADL), and context of daily living (CDL). In an additional aspect, well-being may include the alleviation of adverse impacts upon a person's medical condition, emotional stability, mental stability, physical stability, financial stability, physiological problems, as well as to improve performance in many aspects of life such as daily activities, physical, emotional, mental activities, environmental conditions, and other functions, and also to contribute to the regulation of the various physiological systems of the organism (e.g., person) such as, the immune system. In one aspect, the well-being may be a subjective well-being (SWB) that may be defined as the degree to which people have positive thoughts and feelings about their lives and are often measured through self-reports of life satisfaction. A rating or scaling system may be used. For example, a number system from 1-10 may be used where 10 may indicate the greatest degree of positive thoughts and feelings while a 1 may indicate the least most degree of positive thoughts and feelings. A well-being of a person may be defined, stored, and/or included in a knowledge domain or ontology.

In one aspect, the one or more customized communications further include providing one or more notifications or suggestions to alter current activities of daily living (ADL) of the user, future ADLs of the user, or a combination thereof. As used herein, activities of daily living ("ADL" or "ADLs") may refer to the most common activities that people perform during a day. For example, activities of daily living may include many activities that take place throughout the day, particularly going to work, child-care, elderly care, health management, communication management, financial management, safety/emergency responses, shopping, visiting friends or family, traveling, housekeeping, grooming or personal hygiene practices, meal preparation/dining out, engaging in social media, and even using a computer. ADL may also be used in terms of healthcare to refer to the person's daily self-care activities. The context of daily living ("CDL" or "CDLs") may refer to the context in which one or more ADLs are executed or carried out. The CDL may also include one or more dimensions such as, for example, time, location, environment conditions, weather conditions, traffic conditions, and the like. A knowledge domain may provide one or more correlations or relationships between a person's health state and the ADLs and CDLs.

Some ADLs may also be applicable for one or more types of specific events. For example, a person having experienced a recent surgical procedure may require different or altered ADLs for treatment, recovery, or even resuming previously enjoyed ADLs. Each organism (e.g., person) may have different ADLs than other persons. Accordingly, the ADLs for each person may be learned, identified, and analyzed. In one aspect, the ADLs for a person may be learned such as, for example, using machine learning or using a knowledge domain relating to information about the person's activities and behaviors. The machine learning may provide a predictive model that may analyze, determine, identify, and/or predict any ADL behavior or activity for the user.

In one aspect, the customized communications may include suggestions and interactions with a user using dialogue involving one or more modalities, including the spoken dialogue. The spoken dialogue may comprise one or more audible communications directed at the user or of the user. The component aiding the implementation may control navigation, entertainment, and telecommunication systems in the user's possession and/or associated with the user.

In one aspect, feedback information about the user may be collected from one or more IoT devices or sensors such as, for example, smart phones, wearable devices or sensors (e.g. proximity sensors, cameras, radio frequency identification "RFID" readers, biometric sensors, wearable sensors, and the like.). A stream of feedback data may be processed and the real-time flux of information enables the generation of knowledge or knowledge domain/ontology and enables the learning a health state of a user and generating personalized advice (e.g., suggestions, warnings, alerts, or recommendations) relating to the learned health state for adjusting one or more ADLs, CDLs, or other activities and environments that may negatively impact the person's well-being or state of health, using cloud computing and/or edge computing technology.

Also, as used herein, sensors may include proximity sensors, cameras, radio frequency identification "RFID" readers, biometric sensors, wearable sensors, computers, handheld devices (e.g., Global Positioning System "GPS" device or step counters), smart phones, and/or other sensor based devices.

Accordingly, the "health state" of a particular user may depend greatly upon contextual factors, such as a correlation or relationship between the health state and ADLs/CDLs of the user, and other contextual factors such as defined by a user or learned via artificial intelligence. A deeper, cognitive analysis of the health state of a person (e.g., a patient) may be learned based on, for example, standards, rules, practices, and/or learned ADLs, CDLs, and/or other related behaviors or activities. In short, a cognitive learning process using artificial intelligence may learn each of the actions, decisions, ADLs, CDLs, modes of travel, behavior patterns of a user, a medical profile (which may include data relating to medical care or medical conditions), or other activities. Each learned health state may be saved as part of a user profile and/or retained in a knowledge domain. For example, the cognitive learning may learn preferred ADLs for particular priorities (e.g., brush teeth before leaving to work), preferences (dining at a particular restaurant), or even time periods (e.g., walking to work on warm, sunny days while taking a cab to work on rainy days).

The ontology may include, but is not limited to, the knowledge domain or data repository of a collection of material, information, content and/or other resources related to a particular subject or subjects. For example, the ontology may include, data relating to a user's health state. The ontology may have defined ADLs, CDLs, and a user profile (e.g., calendar information, historical data relating to medical conditions of the user, emotional/physical/mental condition of the user, preferences, priorities, biomedical data, psychophysical parameters of the user, medical history, emotional data, skills set, and the like). The ontology may also have environmental data, traffic data, routes, roads, streets, highways, interstates, trails, bridges, maps, airports, geographical data, medical conditions, nutritional data, weather data, and the like.

One or more machine learning models may be invoked and applied to cognitive learning about the user and/or a health state such as, for example, ADLs, CDLs, priorities, activity preferences, daily or future calendaring, behaviors, skill sets of a user, medical conditions, capabilities, performance capabilities, and/or other types of data needed for providing communications to suggest one or more alterations, adjustments, or planning alternative activities to eliminate or reduce possible adverse impacts on the person's health state.

It should be noted that one or more calculations may be performed using various mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.).

Other examples of various aspects of the illustrated embodiments, and corresponding benefits, will be described further herein.

It is understood in advance that although this disclosure includes a detailed description on cloud computing, implementation of the teachings recited herein are not limited to a cloud computing environment and/or computing systems associated with one or more vehicles. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, system memory 28 may include at least one program product having a set (e.g., at least one) of program modules that are configured to carry out the functions of embodiments of the invention.

Program/utility 40, having a set (at least one) of program modules 42, may be stored in system memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
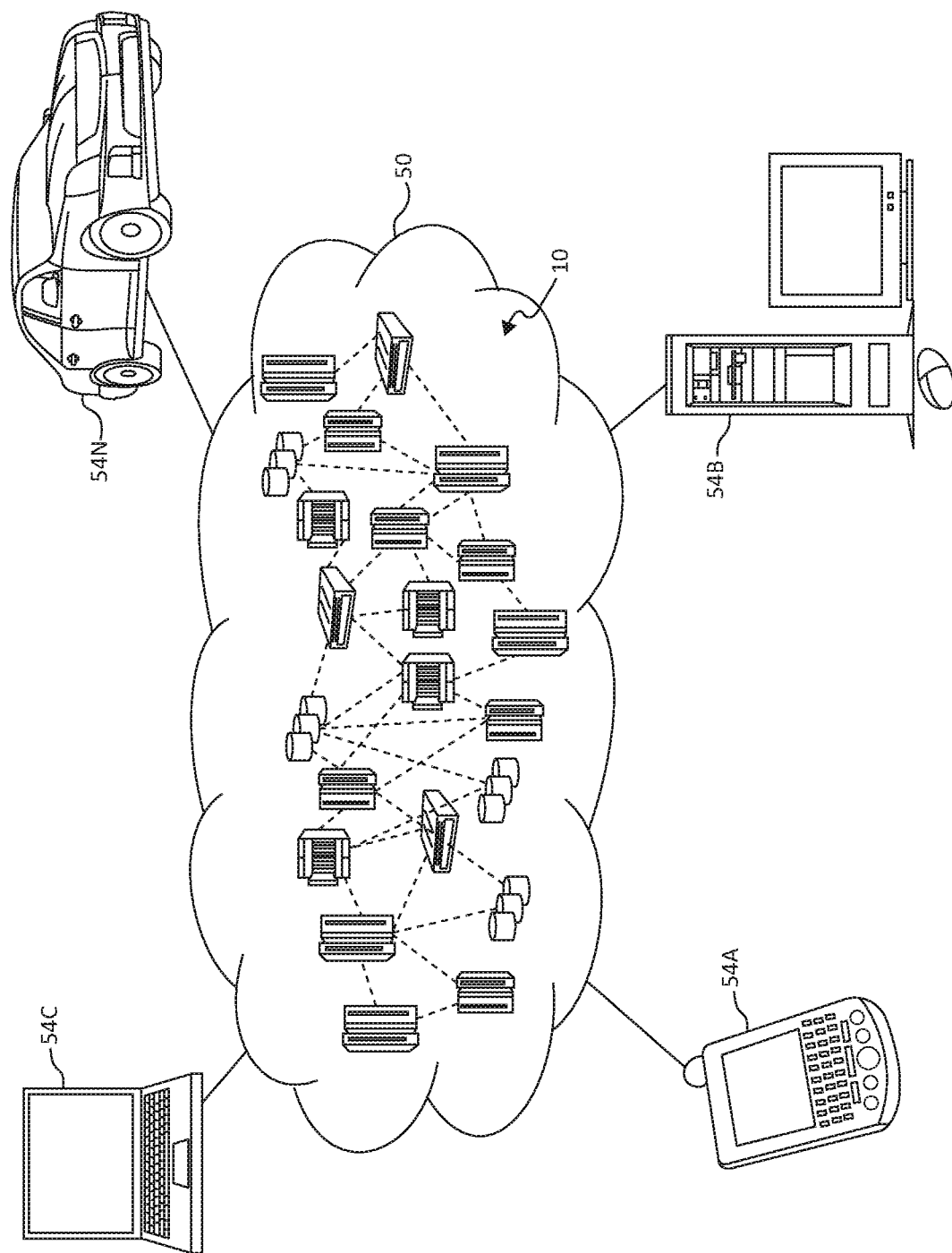
FIG. 2 is an additional block diagram depicting an exemplary cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
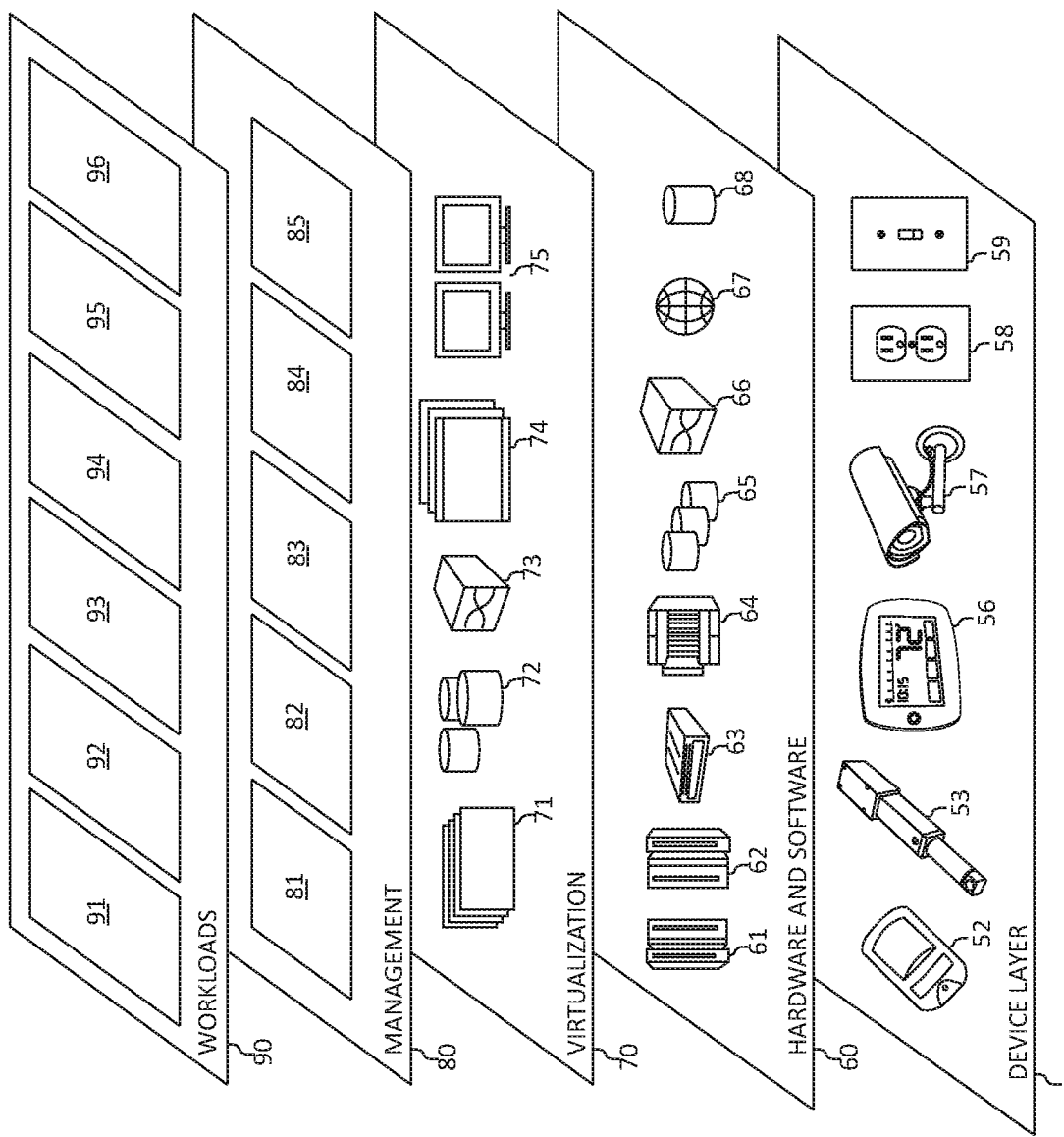
FIG. 3 is an additional block diagram depicting abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Device layer 55 includes physical and/or virtual devices, embedded with and/or standalone electronics, sensors, actuators, and other objects to perform various tasks in a cloud computing environment 50. Each of the devices in the device layer 55 incorporates networking capability to other functional abstraction layers such that information obtained from the devices may be provided thereto, and/or information from the other abstraction layers may be provided to the devices. In one embodiment, the various devices inclusive of the device layer 55 may incorporate a network of entities collectively known as the "internet of things" (IoT). Such a network of entities allows for intercommunication, collection, and dissemination of data to accomplish a great variety of purposes, as one of ordinary skill in the art will appreciate.

Device layer 55 as shown includes sensor 52, actuator 53, "learning" thermostat 56 with integrated processing, sensor, and networking electronics, camera 57, controllable household outlet/receptacle 58, and controllable electrical switch 59 as shown. Other possible devices may include, but are not limited to various additional sensor devices, networking devices, electronics devices (such as a remote-control device), additional actuator devices, so called "smart" appliances such as a refrigerator or washer/dryer, and a wide variety of other possible interconnected objects.

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, in the context of the illustrated embodiments of the present invention, various cognitive health state learning and personalized advice generation workloads and functions 96. In addition, cognitive health state learning and personalized advice generation workloads and functions 96 may include such operations as data analytics, data analysis, and as will be further described, notification functionality. One of ordinary skill in the art will appreciate that the cognitive health state learning and personalized advice generation workloads and functions 96 may also work in conjunction with other portions of the various abstractions layers, such as those in hardware and software 60, virtualization 70, management 80, and other workloads 90 (such as data analytics processing 94, for example) to accomplish the various purposes of the illustrated embodiments of the present invention.

Figure 4:
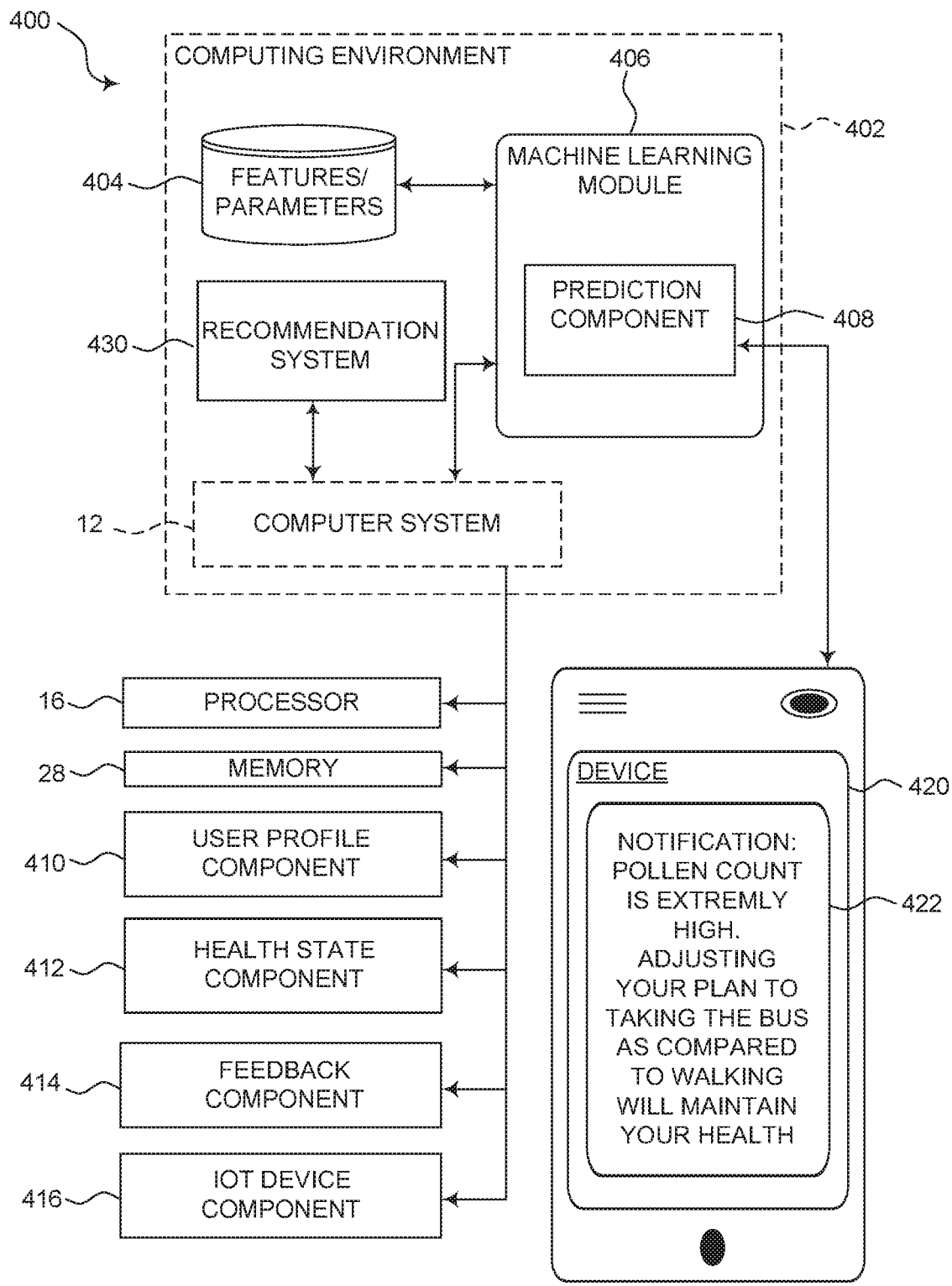
FIG. 4 is a diagram depicting various user hardware and computing components functioning in accordance with aspects of the present invention.

Turning now to FIG. 4, a block diagram depicting exemplary functional components 400 according to various mechanisms of the illustrated embodiments is shown. FIG. 4 illustrates cognitive health state learning and personalized advice generation workloads and functions and training of a machine-learning model in a computing environment, such as a computing environment 402, according to an example of the present technology. As will be seen, many of the functional blocks may also be considered "modules" or "components" of functionality, in the same descriptive sense as has been previously described in FIGS. 1-3. With the foregoing in mind, the module/component blocks 400 may also be incorporated into various hardware and software components of a system for cognitive health state learning and personalized advice generation in accordance with the present invention. Many of the functional blocks 400 may execute as background processes on various components, either in distributed computing components, or on the user device, or elsewhere. Computer system/server 12 is again shown, incorporating processing unit 16 and memory 28 to perform various computational, data processing and other functionality in accordance with various aspects of the present invention.

The system 400 may include the computing environment 402, a recommendation system 430, and a device 420, such as a desktop computer, laptop computer, tablet, smart phone, and/or another electronic device that may have one or more processors and memory. The device 420, the recommendation system 430, and the computing environment 402 may each be associated with and/or in communication with each other, by one or more communication methods, such as a computing network. In one example, the device 420 and/or the recommendation system 430 may be controlled by a user, an owner, customer, patient, health care provider, or administrator associated with the computing environment 402. In another example, the device 420 and/or the recommendation system 430 may be completely independent from the user, owner, customer, patient, health care provider, or administrator of the computing environment 402.

In one aspect, the computing environment 402 may provide virtualized computing services (i.e., virtualized computing, virtualized storage, virtualized networking, etc.) to devices 420. More specifically, the computing environment 402 may provide virtualized computing, virtualized storage, virtualized networking and other virtualized services that are executing on a hardware substrate.

As depicted in FIG. 4, the computing environment 402 may include a machine learning module 406, a features and/or parameters 404 that is associated with a machine learning module 406, and the recommendation system 430. The features and/or parameters may include ADLs, CDLs, health state data, and a knowledge domain/ontology. The features and/or parameters database 404 may also include user profiles (e.g., a patient profile) for the recommendation system 430 and/or IoT devices associated with a IoT device component 416 (e.g., an IoT sensor device, camera, voice activated device, and other types of IoT devices). It should be noted that one or more IoT devices may be represented as the IoT device component 416 may be coupled to the recommendation system 430. The features and/or parameters 404 may be a combination of ADLs, CDLs, features, parameters, rules, behavior characteristics, patient/user profile data, calendaring data, health and nutrition data, physical or mental capabilities, emotional data, medical condition data, nutritional constraint data, health constraint data, historical data, travel related data, child care data, tested and validated data, or other specified/defined data for testing, monitoring, validating, detecting, learning, analyzing and/or calculating various conditions or diagnostics relating to cognitively learning the health state of a user for providing personalized advice, warnings, or suggestions to adjust one or more ADLs to avoid adverse impacts on the user's health state in the recommendation system 430. That is, different combinations of ADLs, CDLs, features, or parameters may be selected and applied to the input data for learning or training one or more machine learning models of the machine learning module 406. The features and/or parameters 404 may define one or more settings of an IoT device (e.g., IoT device 420) associated with the IoT device component 416 to enable the IoT device 420 to interact with a member or user of the IoT device 420 and the computer system 12. The IoT device component 416 may be associated with the recommendation system 430 and the IoT device 420.

The computing environment 402 may also include a computer system 12, as depicted in FIG. 1. The computer system 12 may also include the user profile component 410, a health state component 412, a feedback component 414, and the IoT device component 416 each associated with the machine learning module for training and learning one or more machine learning models and also for applying multiple combinations of ADLs, CDLs, features, parameters, behavior patterns or characteristics, patient/user profile data, historical data, or a combination thereof to the machine learning model for use in the recommendation system 430 for cognitively learning a health state of a user and recommending personalized advice, suggestions, or notifications relating to the learned health state to avoid possible negative impacts upon the health state of a user/patient.

In one aspect, the machine learning module 406 may include a prediction component 408 for cognitively learning a health state of a user and recommending personalized advice, suggestions, or notifications of a user/patient profile, by one or more IoT devices 420 associated with the IoT device component 416 in the recommendation system 430.

The user profile component 410 may include data relating to a health state of a user (e.g., the well-being of the user), ADLs, CDLs, behavioral patterns and characteristics, feedback information, and data associated with the knowledge domain/ontology. Each specific state, condition, or element of the health state of the user may be ranked and organized by priority (e.g., highest numerical value indicates a stronger preference or like while lower numerical values indicate a dislike or disapproval, or vice versa). For example, an emotional state of the user may be assigned a value of 10 (e.g., the user is extremely happy, satisfied, or comfortable). On the other hand, the physical capabilities of the user may be assigned a value of 5 indicating neutral or neither happy, satisfied, or comfortable based on a recent surgical procedure. In short, both the overall well-being of the user may be provided a score or ranking while also ranking and scoring each of the various components, elements, states, or conditions that are included in the overall well-being of the user.

The computer system 12 may use a health state component 412 to cognitively determine the level of the well-being or health state of the user for each ADL and CDL. The health state component 412 may use the user profile component 410 to collect, gather, calculate, and cognitively determine the well-being/health state. Also, the health state component 412 may use the one or more IoT device components 416 to cognitively determine the well-being/health state such as, for example, by collecting biometric data, body motions, and the like such as via a hand (a hand gesture covering the facial area and facial movement detecting a sneeze or cough) or face gesture (e.g., a smile or frown), or one or more communication messages to a social media network (e.g., the member shares a picture of a common ADL and/or CDL with a "like" and comment stating "I love walking to work in the spring when the weather is so warm").

A feedback component 414 may use a variety of feedback information relating to the recommendation system 430 and feedback information pertaining to the user may be stored and maintained in the feedback component 414 and used by the machine learning module 406, the features and/or parameters 404, or both. The feedback component 414 may collect a variety of feedback information for the user/patient. For example, the feedback component 414 may collect data gathered from the user (e.g., cognitive interaction and reasoning), an IoT device 420, or other source for learning a health state of a user and generating personalized advice to avoid adverse impacts on the person's health state/well-being.

Additionally, the machine learning module 406, in conjunction with the prediction component 408, may use the feedback information to cognitively learn a health state/well-being of a user and recommend one or more customized communications to the user to alter one or more activities of the user so as to avoid one or more possible negative impacts upon the health state/well-being of the user in the recommendation system 430.

Also, the device 420 may include a graphical user interface (GUI) 422 enabled to display on the device 420 one or more user interface controls for a user to interact with the GUI 422. For example, the GUI 422 may display one or more customized communications to a user to alter one or more activities of the user so as to avoid one or more possible negative impacts upon the health state of the user via an interactive graphical user interface (GUI). For example, the one or more customized communications may indicate or display audibly and/or visually on the GUI 422 "Notification: Pollen count is extremely high. Adjusting your plan to taking the bus as compared to walking will maintain your health (e.g., avoiding an allergy attack for the user suffering from allergies relating to pollen)." The message notification on the GUI 422 may vary, change, and be updated according to real time feedback received from the feedback component 414. Also, the message notification on the GUI 422 may be a series of interactive messages between a user of the IoT device 420 and the computing environment 402.

In one aspect, cognitively learning a health state of a user and generating personalized advice and estimation/predictive modeling (or machine learning modeling), as described herein, may be performed using a wide variety of methods or combinations of methods, such as supervised learning, unsupervised learning, temporal difference learning, reinforcement learning and so forth. Some non-limiting examples of supervised learning which may be used with the present technology include AODE (averaged one-dependence estimators), artificial neural network, backpropagation, Bayesian statistics, naive bays classifier, Bayesian network, Bayesian knowledge base, case-based reasoning, decision trees, inductive logic programming, Gaussian process regression, gene expression programming, group method of data handling (GMDH), learning automata, learning vector quantization, minimum message length (decision trees, decision graphs, etc.), lazy learning, instance-based learning, nearest neighbor algorithm, analogical modeling, probably approximately correct (PAC) learning, ripple down rules, a knowledge acquisition methodology, symbolic machine learning algorithms, sub symbolic machine learning algorithms, support vector machines, random forests, ensembles of classifiers, bootstrap aggregating (bagging), boosting (meta-algorithm), ordinal classification, regression analysis, information fuzzy networks (IFN), statistical classification, linear classifiers, fisher's linear discriminant, logistic regression, perceptron, support vector machines, quadratic classifiers, k-nearest neighbor, hidden Markov models and boosting. Some non-limiting examples of unsupervised learning which may be used with the present technology include artificial neural network, data clustering, expectation-maximization, self-organizing map, radial basis function network, vector quantization, generative topographic map, information bottleneck method, IBSEAD (distributed autonomous entity systems based interaction), association rule learning, apriori algorithm, eclat algorithm, FP-growth algorithm, hierarchical clustering, single-linkage clustering, conceptual clustering, partitional clustering, k-means algorithm, fuzzy clustering, and reinforcement learning. Some non-limiting example of temporal difference learning may include Q-learning and learning automata. Specific details regarding any of the examples of supervised, unsupervised, temporal difference or other machine learning described in this paragraph are known and are within the scope of this disclosure. Also, when deploying one or more machine learning models, a computing device may be first tested in a controlled environment before being deployed in a public setting. Also even when deployed in a public environment (e.g., external to the controlled, testing environment), the computing devices may be monitored for compliance.

In one aspect, the computing system 12/computing environment 402 may perform one or more calculations according to mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.) Thus, as used herein, a calculation operation may include all or part of the one or more mathematical operations.

Figure 5:
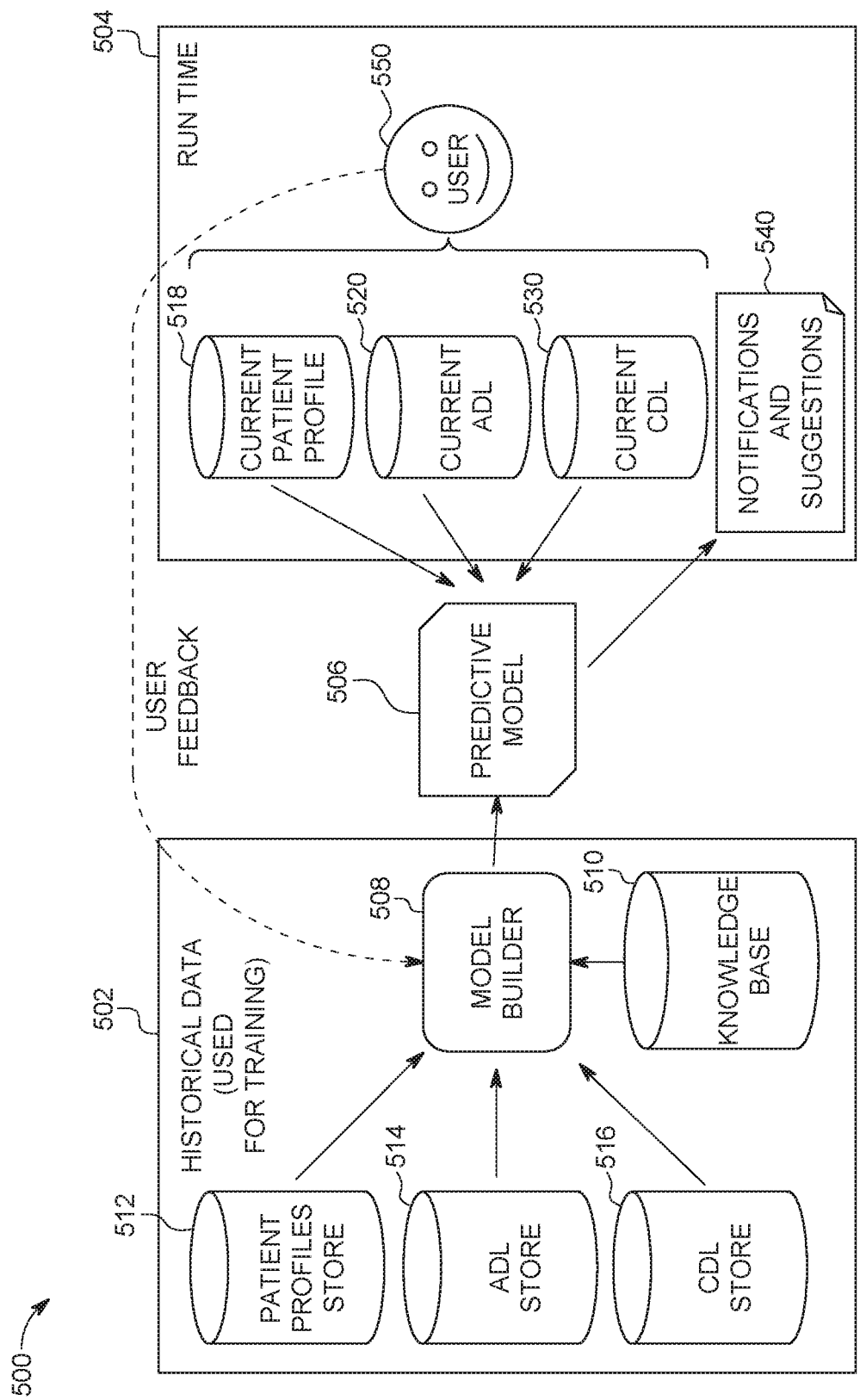
FIG. 5 is an additional block diagram depicting an exemplary functional relationship between various aspects of the present invention.

Turning now to FIG. 5, a block diagram of exemplary functionality 500 of a cognitive health state learning and personalized advice generation system is depicted. It should be noted that the cognitive health state learning and personalized advice generation system may be included in and/or associated with computer system/server 12 of FIG. 1, incorporating one or more processing unit(s) 16 to perform various computational, data processing and other functionality in accordance with various aspects of the present invention.

As shown, the various blocks of functionality are depicted with arrows designating the blocks' 500 relationships with each other and to show process flow of the cognitive health state learning and personalized advice generation system 500. Additionally, descriptive information is also seen relating each of the functional blocks 500. As will be seen, many of the functional blocks may also be considered "modules" or "components" of functionality, in the same descriptive sense as has been previously described in FIGS. 1-4. With the foregoing in mind, the module blocks 500 may also be incorporated into various hardware and software components of a system for image enhancement in accordance with the present invention. Many of the functional blocks 500 may execute as background processes on various components, either in distributed computing components, or on the user device, or elsewhere, and generally unaware to the user performing generalized tasks of the present invention.

In one aspect, user feedback (shown in FIG. 5 as a dotted line from the user 550) may be provided from a user 550 to a predictive model builder 508 ("model builder"), which may occur during run time 504 of a cognitive health state learning and personalized advice generation system. The user feedback may be received by one or more sensors, wearable or implantable devices, a variety of IoT devices (e.g., smart phones, cameras, interactive voice recognition devices, and the like), or other type of device to mine and gather intentions and conditions of the user 550 that may be included in an ADL store 514 and a CDL store 516, or even a knowledge base 510, which may be included or associated with a computing environment 502 for storing, accessing, using, or maintaining historical data that may be used for training (e.g., training the predictive model builder 508). The user feedback may include data relating to a current patient profile(s) 518, current ADL 520, current CDL 530, or a combination thereof.

One or more models such as, for example, predictive model builder 508 may be built, created, organized, stored and maintained for use by a predictive model 506. The predictive model 506 may use and access a patient's profile (e.g., a user profile) that may be maintained in a patient profiles store 512. The knowledge base 510 may also be used to collect information relating to a knowledge domain/ontology discussing various relationships with ADLs/CDLs with the health state. Also, ADL and CDL information may be stored in the ADL store 514 and the CDL store 516. Together, the ADL, CDL, user profile, and feedback information may be used by the predictive model for learning a health state of a user from feedback information collected from one or more sources (e.g., an IoT device). In other words, the feedback information may be augmented with ADL data, CDL data, user profile data, other selected data, or a combination thereof. In this way, the predictive model 506 learns the health state of a user using the feedback information, a health state profile of the user, one or more ADLs of the user, CDLs of the user, or a combination thereof in the predictive model 506.

The predictive model 506 may implement a set or series of rules for using a predictive model. In one aspect, each rule of the set of rules may map a feature vector to a suggestion or notification. The feature vector may indicate and specify an ADL with a CDL for a user. That is, the feature vector may indicate and specify an ADL that may be currently happening in a selected or specific CDL for the user/patient with a medical condition. In other words, the predictive model 506 may collect current patient profile(s) 518 or current ADLs 520 and current CDLs 530 to provide one or more notifications and suggestions 540 to a user to update, change, alter, or recommend current ADLs 520 and current CDLs 530 (or future ADLs or future CDLs) of the user so as to avoid one or more possible negative impacts upon the health state of the user. Over time, the predictive model 506 may fine tune or "improve" the type of notifications and suggestions 540 provided to the user 550. In this way, the predictive model 506 may adjust future customized communications according to updated feedback information.

Figure 6:
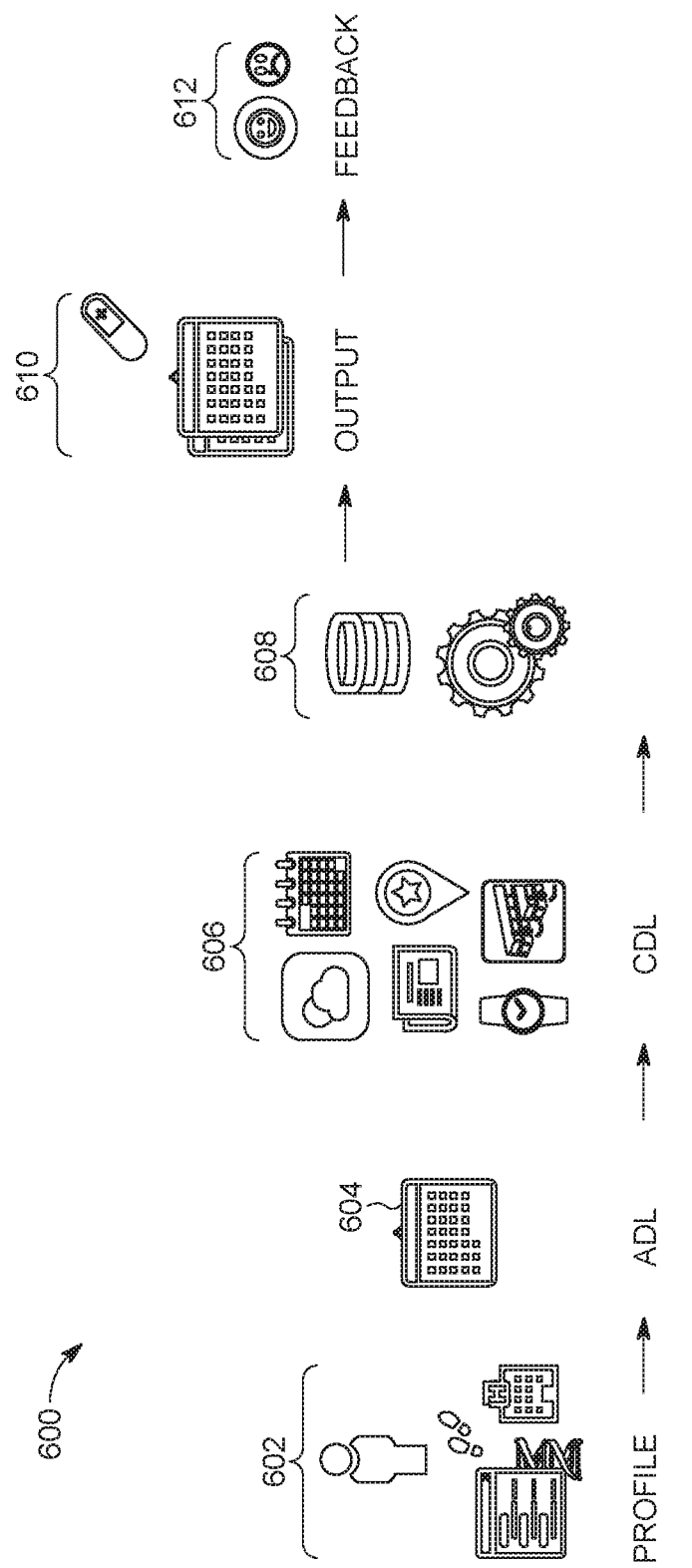
FIG. 6 is an additional block diagram depicting an exemplary functional relationship between various aspects of the present invention.

Turning now to FIG. 6, a block diagram of exemplary functionality 600 of a cognitive health state learning and personalized advice generation system is depicted. It should be noted that the cognitive health state learning and personalized advice generation system may be included in and/or associated with computer system/server 12 of FIG. 1, incorporating one or more processing unit(s) 16 to perform various computational, data processing and other functionality in accordance with various aspects of the present invention.

As shown, the various blocks of functionality are depicted with arrows designating the blocks' 600 relationships with each other and to show process flow of the cognitive health state learning and personalized advice generation system 600. Additionally, descriptive information is also seen relating each of the functional blocks 600. As will be seen, many of the functional blocks may also be considered "modules" or "components" of functionality, in the same descriptive sense as has been previously described in FIGS. 1-5. With the foregoing in mind, the module blocks 600 may also be incorporated into various hardware and software components of a system for image enhancement in accordance with the present invention. Many of the functional blocks 600 may execute as background processes on various components, either in distributed computing components, or on the user device, or elsewhere, and generally unaware to the user performing generalized tasks of the present invention.

Starting with block 602, a user profile may be used to identify a user. For example, the user may be a 50-year-old male user (e.g., patient) with a vestibular disorder (e.g., inner ear disorder) without hypertension. As descriptive block 604 indicates, a calendar may be used that shows, for example, a bus trip planned for the user on the next day. The CDL 606 reveals the trip on the bus may be relatively long, with weather pressure changes as the bus route encounters high altitudes and elevation changes. The predictive model system 608 may be used for outputting one or more notifications or suggestions to the user to alter one or more ADLs or CDLs, as shown in block 610. Feedback information 612 may be collected and gathered to assist the predictive model system 608 to learn the health state of the user. That is, the predictive model system 608 may be used for providing outputs 610 and collecting feedback information 612. The predictive model system 608 may use historical data, feedback information 612, and both the ADL 604 and CDL 606 to learn the health state of the user and the provide one or more customized and personalized notifications or suggestions to the user to alter one or more current ADLs and current CDLs. Also, the feedback information 612 may include feedback data from persons having similar ADLs, CDLs, medical conditions, health states, user profiles, or a combination thereof.

For example, during a learning phase, the predictive model system 608 may cognitively interact with the user. One or more communications may be provided via an interactive GUI, a voice detection device, image/video detection device, video system, camera system, or other IoT device. For example, a message or audible communication may be provided to the user asking a series of questions such as, for example, "Did you like the bus trip?" The user may then audibly, visually, or a combination thereof provide a communication message indicating "No" (e.g., email, text, audio communication, video communication, or an indication in an interactive GUI). The negative response may prompt the predictive model system 608 to ask a second question such as, for example, "What was the most unpleasant part of the trip?" The user may then audibly, visually, or a combination thereof provide a communication message indicating "There were a lot of unpleasant turns." The feedback information 612 may then prompt the predictive model system 608 to ask, "How could this trip be improved?" The user may indicate back to the predictive model system 608 via one or more communication means "I would sit in the front row."

Using this feedback information 612, the predictive model system 608 may data mine the ADL and CDL data, retrieve previous history and feedback information from the user and from similar persons relating to the user as per the ADLs, CDLs, medical conditions, or user profiles. The predictive model system 608 may provide one or more alerts/notifications, recommendations to change plans, recommendations to keep/maintain current plans, or a combination thereof. For example, the one or more alerts/notifications may include ADL or CDL information or alerts notifying the user of changes to the barometric pressure and varying levels of altitude that may likely (e.g., greater than a defined percentage such as 50%) affect people with the user's medical condition. The one or more alerts/notifications may also include the CDL that the bus trip may be long, both in distance and time. The recommendations for the user to change plans may include, for example, recommendations to travel by train to avoid the weather and altitude changes or even postponing the trip by one extra day as the weather forecast predicts improvement in the weather thereby avoiding any negative impacts to the user's medical condition or well-being. The customized or personalized recommendations, for example, to the user to maintain the current plans may include, for example, recommendations to take a nasal decongestion to assist with barometric pressure changes, since the user does not experience hypertension. Also, a recommendation for keeping the current plan may include a suggestion to travel with another companion, associate, friend, family member, or other person. In short, the recommendations may be customized, personalized, or adapted for each user according to the learned health state/well-being of each user.

The user may also rate or score the recommendation(s) in additional feedback information to extend or increase the knowledge base and calibrate or adjust the predictive model system 608 to improve the customization process of providing recommendations. Also, feedback from other patients having similar conditions, ADLs, CDLs, or a combination thereof may be used to learn or acquire new intelligence or "insights" for the customization process of providing recommendations (e.g., sit in the front row of the bus is data that enhances the artificial intelligence or machine learning for someone taking the bus with the user's condition).

Consider the following examples of an implementation of the aforementioned functionality where the cognitive health state learning and personalized advice generation system is employed. In one example, assume that a pollen count (e.g., an allergen that a person is allergic to as indicated in the person profile) is high for the current time and location period. Assume that the usual daily activity (ADL) for that person for that day of the week is a 5 kilometers run ("5K run") in a park. The personalized suggestions and notifications, based on the learned health state of the user, may be to adjust the 5K run from outdoors to running the 5K on a treadmill in a local gym where the user frequents. Alternatively, the customized communication to the user may indicate taking an allergy medicine best suited to this person for this situation.

As an additional example, assume a person has a blood condition with a high number of red cells (Polycythemia vera) and is planning to travel. The travel itinerary of the user indicates one short-time duration flight (e.g., less than 2 hours) and one long-time duration flight (e.g., greater than 2 hours). Accordingly, personalized suggestions and notifications, based on the learned health state of the user, may be to suggest or reason with the person to try to amend the itinerary to the short-time duration flights or even schedule an appointment with a physician/doctor to receive blood thinning injections for the travel.

As an additional example, assume a person has diving activities (ADL) today and the calendar of the person shows a flight home the next morning. Accordingly, the personalized suggestions and notifications, based on the learned health state of the user, may be to issue a warning about health threatening activities and advise to postpone the flight.

Figure 7:
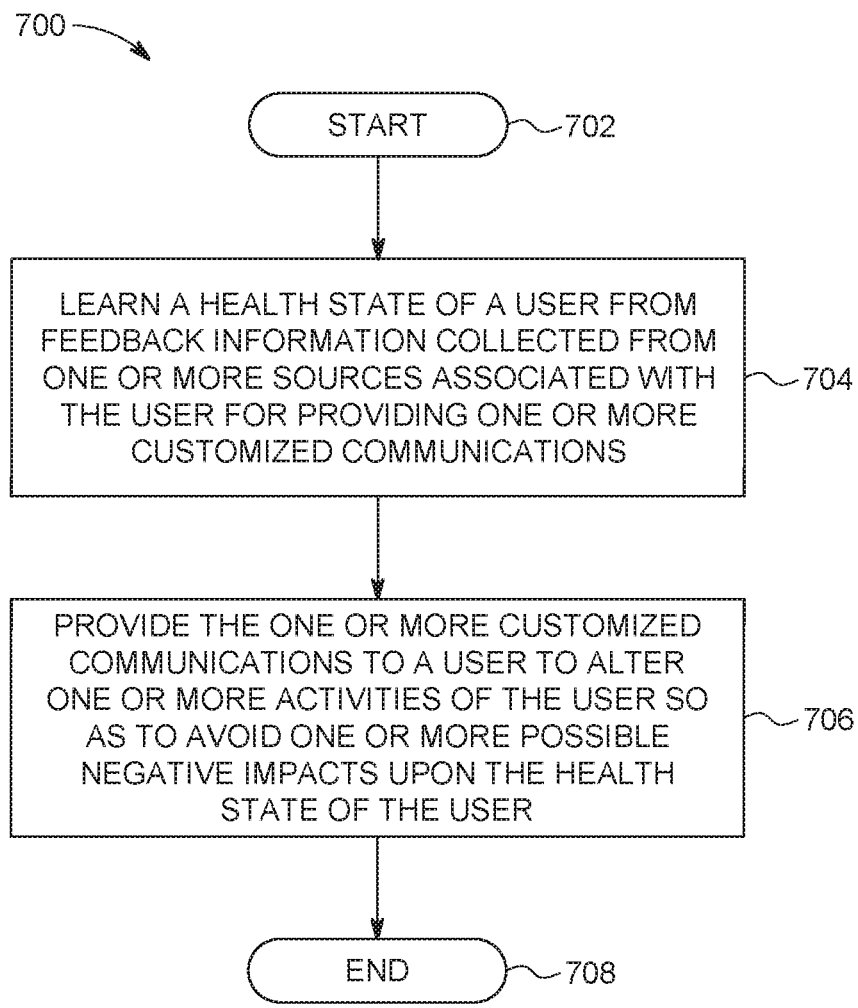
FIG. 7 is an additional flowchart diagram depicting an additional exemplary method for learning a health state of a user and generating personalized advice by a processor, again in which aspects of the present invention may be realized.

Turning now to FIG. 7, a method 700 for generating personalized advice by a processor is depicted, in which various aspects of the illustrated embodiments may be implemented. The functionality 700 may be implemented as a method executed as instructions on a machine, where the instructions are included on at least one computer readable medium or one non-transitory machine-readable storage medium. The functionality 700 may start in block 702. A health state of a user is learned from feedback information collected from a plurality of data sources for providing one or more customized communications, as in block 704. One or more customized communications may be provided to a user to alter one or more activities of the user so as to avoid one or more possible negative impacts upon the health state of the user, as in block 706. The functionality 700 may end, as in block 708.

In one aspect, in conjunction with and/or as part of at least one block of FIG. 7, the operations of method 700 may include each of the following. The operations of method 700 may cognitively reason and interact with the user for collecting the feedback information.

In an additional aspect, the operations of method 700 may also include initializing a machine learning mechanism using the feedback information to learn the health state. The health state may include at least one or more medical conditions, a subjective well-being (SWB) of the user, an emotional state of the user, biometric data, behavior patterns, a health profile of the user, or a combination thereof.

The operations of method 700 may provide one or more notifications or suggestions in the customized communication to the user to alter current ADLs of the user, future ADLs of the user, or a combination thereof.

Moreover, the operations of method 700 may implement a set of rules for using a predictive model. The feedback information, a health state profile of the user, one or more ADLs of the user, CDLs, or a combination thereof may be used in the predictive model. The user feedback may also be augmented with information from a knowledge domain that describes correlations between the health state, ADL, CDL, or a combination thereof of the user.

The operations of method 700 may adjust future customized communications according to updated feedback information, adjust one or more ADLs, one or more CDLs, or a combination thereof based on the customized communications.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowcharts and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The invention claimed is:

1. A method for cognitive health state learning and personalized advice generation by a processor, comprising:
   receiving, through an interface of a computing device incorporating the processor, a plurality of health data of a user, wherein the plurality of health data is representative of feedback information collected from one or more sources associated with the user;
   executing machine learning logic, using the feedback information as input, to learn a health state of the user, wherein the machine learning logic generates one or more customized communications related to the health state of the user;
   identifying, by the machine learning logic, components associated with current activities of daily living (ADL) and planned future ADL of the user;
   dividing, by the machine learning logic, the components of a respective planned future ADL the user is scheduled to engage in into a plurality of sub-components, wherein one of the components is a method of travel and one of the plurality of sub-components is associated with a route of travel;
   determining, by the machine learning logic, that the route of travel associated with the respective planned future ADL consists of a controllable element having an uncontrollable condition predicted to temporarily change according to environmental factors during a course of movement of the user as the user engages in the respective planned future ADL, above a predetermined threshold, that would adversely affect a specific health condition of the user according to the health data; and
   providing on the interface, according to output of the machine learning logic, the one or more customized communications to the user to alter one or more of the current ADL and the future planned ADL of the user so as to avoid one or more possible negative impacts upon the health state of the user, wherein providing the one or more customized communications includes providing one or more notifications to the user recommending to modify at least one of the plurality of sub-components of the components of the respective planned future ADL.

2. The method of claim 1, further including cognitively reasoning and interacting with the user for collecting the feedback information.

3. The method of claim 1, wherein the health state includes at least one or more medical conditions, a subjective well-being (SWB) of the user, an emotional state of the user, biometric data, behavior patterns, a health profile of the user, or a combination thereof.

4. The method of claim 1, further including:
   implementing a series of rules for using a predictive model; and using the feedback information, a health state profile of the user, one or more of the current ADL of the user, context of daily living (CDL), or a combination thereof in the predictive model.

5. The method of claim 1, further including augmenting the user feedback with information from a knowledge domain that describes correlations between the health state, the current ADL, context of daily living (CDL), or a combination thereof of the user.

6. The method of claim 1, further including adjusting future customized communications according to updated feedback information.

7. The method of claim 1, further including adjusting one or more of the ADL, one or more contexts of daily living (CDL), or a combination thereof based on the customized communications.

8. A system for generating personalized advice, comprising:
one or more computers with executable instructions that when executed cause the system to:
receive, through an interface of the one or more computers, a plurality of health data of a user, wherein the plurality of health data is representative of feedback information collected from one or more sources associated with the user;
execute machine learning logic, using the feedback information as input, to learn a health state of the user, wherein the machine learning logic generates one or more customized communications related to the health state of the user;
identify, by the machine learning logic, components associated with current activities of daily living (ADL) and planned future ADL of the user;
divide, by the machine learning logic, the components of a respective ADL the user is scheduled to engage in into a plurality of sub-components, wherein one of the components is a method of travel and one of the plurality of sub-components is associated with a route of travel;
determine, by the machine learning logic, that the route of travel associated with the respective planned future ADL consists of a controllable element having an uncontrollable condition predicted to temporarily change according to environmental factors during a course of movement of the user as the user engages in the respective planned future ADL, above a predetermined threshold, that would adversely affect a specific health condition of the user according to the health data; and
provide, according to output of the machine learning logic, the one or more customized communications to the user to alter one or more of the current ADL and the future planned ADL of the user so as to avoid one or more possible negative impacts upon the health state of the user, wherein providing the one or more customized communications includes providing one or more notifications to the user recommending to modify at least the respective sub-component of the components of the respective ADL.

9. The system of claim 8, wherein the executable instructions further cognitively reason and interact with the user for collecting the feedback information.

10. The system of claim 8, wherein the health state includes at least one or more medical conditions, a subjective well-being (SWB) of the user, an emotional state of the user, biometric data, behavior patterns, a health profile of the user, or a combination thereof.

11. The system of claim 8, further including:
implementing a series of rules for using a predictive model; and
using the feedback information, a health state profile of the user, one or more of the current ADL of the user, context of daily living (CDL), or a combination thereof in the predictive model.

12. The system of claim 8, further including augmenting the user feedback with information from a knowledge domain that describes correlations between the health state, the current ADL, context of daily living (CDL), or a combination thereof of the user.

13. The system of claim 8, further including:
adjusting future customized communications according to updated feedback information; or
adjusting one or more of the ADLs, one or more contexts of daily living (CDL), or a combination thereof based on the customized communications.

14. A computer program product for generating personalized advice to a user, by a processor, the computer program product comprising a non-transitory computer-readable storage medium having computer-readable program code portions stored therein, the computer-readable program code portions comprising:
an executable portion that receives, through an interface of a computing device incorporating the processor, a plurality of health data of a user, wherein the plurality of health data is representative of feedback information collected from one or more sources associated with the user;
an executable portion that executes machine learning logic, using the feedback information as input, to learn a health state of the user, wherein the machine learning logic generates one or more customized communications related to the health state of the user;
an executable portion that identifies, by the machine learning logic, components associated with current activities of daily living (ADL) and planned future ADL of the user;
an executable portion that divides, by the machine learning logic, the components of a respective ADL the user is scheduled to engage in into a plurality of sub-components, wherein one of the components is a method of travel and one of the plurality of sub-components is associated with a route of travel;
an executable portion that determines, by the machine learning logic, that the route of travel associated with the respective planned future ADL consists of a controllable element having an uncontrollable condition predicted to temporarily change according to environmental factors during a course of movement of the user as the user engages in the respective planned future ADL, above a predetermined threshold, that would adversely affect a specific health condition of the user according to the health data; and
an executable portion that provides, according to output of the machine learning logic, the one or more customized communications to the user to alter one or more of the current ADL and the future planned ADL of the user so as to avoid one or more possible negative impacts upon the health state of the user, wherein providing the one or more customized communications includes providing one or more notifications to the user recommending to modify at least the respective sub-component of the components of the respective ADL.

15. The computer program product of claim 14, further including an executable portion that cognitively reasons and interacts with the user for collecting the feedback information.

16. The computer program product of claim 14, wherein the health state includes at least one or more medical conditions, a subjective well-being (SWB) of the user, an emotional state of the user, biometric data, behavior patterns, a health profile of the user, or a combination thereof.

17. The computer program product of claim 14, further including an executable portion that:
- implements a series of rules for using a predictive model; and
- uses the feedback information, a health state profile of the user, one or more of the current ADL of the user, context of daily living (CDL), or a combination thereof in the predictive model.

18. The computer program product of claim 14, further including an executable portion that:
- augments the user feedback with information from a knowledge domain that describes correlations between the health state, the current ADL, context of daily living (CDL), or a combination thereof of the user;
- adjusts one or more of the ADL, one or more contexts of daily living (CDL), or a combination thereof based on the customized communications; or adjusts future customized communications according to updated feedback information.

* * * * *